(12) United States Patent
DiMatteo et al.

(10) Patent No.: US 8,465,538 B2
(45) Date of Patent: Jun. 18, 2013

(54) VARIABLE LENGTH ENDOVASCULAR GRAFT PROSTHESIS ADAPTED TO PREVENT ENDOLEAKS

(75) Inventors: Kristian J. DiMatteo, Waltham, MA (US); Robert C. Thistle, Bridgewater, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 346 days.

(21) Appl. No.: 12/820,777

(22) Filed: Jun. 22, 2010

(65) Prior Publication Data

US 2010/0256745 A1 Oct. 7, 2010

Related U.S. Application Data

(62) Division of application No. 11/090,522, filed on Mar. 25, 2005, now Pat. No. 7,766,959.

(51) Int. Cl.
*A61F 2/06* (2006.01)

(52) U.S. Cl.
USPC ........................................... 623/1.16

(58) Field of Classification Search
USPC ............... 623/1.13, 1.16, 1.27, 1.28, 1.44
See application file for complete search history.

(56) References Cited

U.S. PATENT DOCUMENTS

| 4,728,328 | A | 3/1988 | Hughes et al. |
| 5,064,435 | A | 11/1991 | Porter |
| 5,156,620 | A | 10/1992 | Pigott |
| 5,755,770 | A | 5/1998 | Ravenscroft |
| 5,899,913 | A | * | 5/1999 | Fogarty et al. ............... 606/159 |
| 6,102,940 | A | | 8/2000 | Robichon et al. |
| 6,129,756 | A | | 10/2000 | Kugler et al. |
| 6,152,956 | A | | 11/2000 | Pierce |
| 6,221,102 | B1 | | 4/2001 | Baker et al. |
| 6,287,335 | B1 | | 9/2001 | Drasler et al. |
| 6,303,100 | B1 | | 10/2001 | Ricci et al. |

(Continued)

FOREIGN PATENT DOCUMENTS

| FR | 1526295 | 5/1968 |
| WO | 97/09008 | 3/1997 |

(Continued)

OTHER PUBLICATIONS

International Search Report and Written Opinion from related PCT Application No. PCT/US2006/010652, dated Jun. 28, 2006.

(Continued)

*Primary Examiner* — Gary Jackson
*Assistant Examiner* — Martin Ton
(74) *Attorney, Agent, or Firm* — Brooks, Cameron & Huebsch, PLLC

(57) ABSTRACT

A variable length endovascular prosthesis to prevent endoleaks includes a substantially tubular first graft member having an interior surface, an exterior surface, and an open end, and a substantially tubular second graft member engaged coaxially within the first graft member, the second graft member having a proximal end. The prosthesis further includes a substantially tubular fluid-tight connecting member attached at one end to the first graft member and attached at another end to the second graft member, where the connecting member is axially compressible and expandable to facilitate engagement of the proximal end of the second graft member within the first graft member while maintaining a seal between the proximal end of the second graft member and the open end of the first graft member.

22 Claims, 3 Drawing Sheets

U.S. PATENT DOCUMENTS

| | | | |
|---|---|---|---|
| 6,325,823 B1 * | 12/2001 | Horzewski et al. | 623/1.16 |
| 6,451,051 B2 * | 9/2002 | Drasler et al. | 623/1.15 |
| 7,226,474 B2 | 6/2007 | Iancea et al. | |
| 2002/0052644 A1 | 5/2002 | Shaolian et al. | |
| 2003/0068296 A1 | 4/2003 | Ricci et al. | |
| 2003/0236567 A1 | 12/2003 | Elliot | |

FOREIGN PATENT DOCUMENTS

| | | |
|---|---|---|
| WO | 97/17910 | 5/1997 |
| WO | 2004/017867 A1 | 3/2004 |
| WO | 2006028925 A1 | 3/2006 |

OTHER PUBLICATIONS

A Canadian Office Action in related Canadian Patent Application No. 2,602,909. Sep. 12, 2012. 4 pgs.

* cited by examiner

VARIABLE LENGTH ENDOVASCULAR GRAFT PROSTHESIS ADAPTED TO PREVENT ENDOLEAKS

CROSS-REFERENCE TO RELATED APPLICATIONS

This application is a divisional of U.S. patent application Ser. No. 11/090,522, filed Mar. 25, 2005, which is herein incorporated by reference.

BACKGROUND OF THE INVENTION

Endovascular graft prostheses are typically used, for example, in the treatment of abdominal aortic aneurysms (AAAs). Once placed, such prostheses must conform to changing vessel morphology. A prosthesis comprised of modular components which are movable relative to one another may provide for such conformation, but leakage between the modular components must be avoided. Fluid leakage at the connection between modular components is termed in the art as an endoleak.

Endoleaks may result from poor integrity at a connection, either as initially installed or subsequently, when the lumen within which the prosthesis is located shrinks and/or kinks or straightens, frequently resulting in modular component separation and/or leakage.

Accordingly, there remains a need for a flexible, variable length endovascular prosthesis in which endoleaks are avoided.

SUMMARY OF THE INVENTION

A variable length endovascular graft prosthesis is adapted to prevent endoleaks. In one embodiment, the prosthesis includes a substantially tubular first graft member and a substantially tubular second graft member engaged coaxially within the first graft member. A substantially tubular fluid-tight connecting member is attached at one end to the first graft member and attached at another end to the second graft member. The connecting member is axially compressible and expandable to facilitate variable length engagement of the second graft member within the first graft member while maintaining a seal between the graft members. The first and second graft members may include, for example, grafts, stent-grafts, or a combination thereof.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figures 1A, 1B:
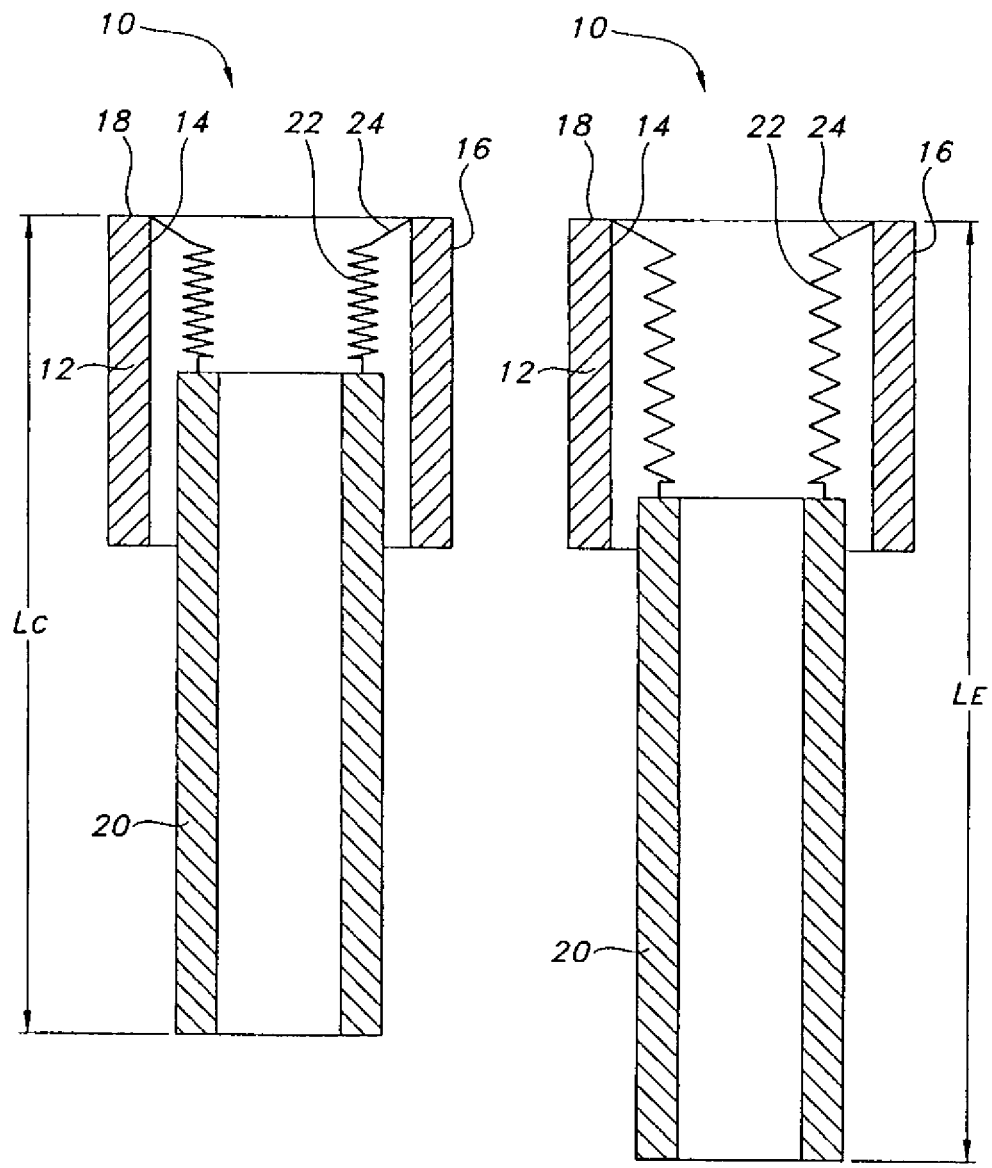
FIG. 1A is a cross-sectional view of an endovascular prosthesis comprised of two coaxially engaged graft members, in a compressed configuration, illustrating a pleated connecting member residing within a first graft member.
FIG. 1B is a cross-sectional view of the embodiment illustrated in FIG. 1A, showing the endovascular prosthesis in an expanded configuration.

Referring generally to FIGS. 1A and 1B, there is shown a variable length endovascular prosthesis 10 adapted to prevent endoleaks. Prosthesis 10 includes a substantially tubular first graft member 12 having an interior surface 14, an exterior surface 16, and a proximal end 18, and a substantially tubular second graft member 20 engaged coaxially within the first graft member 12. Prosthesis 10 further includes a substantially tubular fluid-tight connecting member 22 attached at one end to the first graft member 12 and attached at another end to the second graft member 20. Connecting member 22 is axially compressible and expandable to facilitate variable length engagement of the second graft member 20 within the first graft member 12 while maintaining a seal between the graft members 12, 20.

Connecting member 22 is formed from graft material of the second graft member 20 and is attached at a free end 24 to interior surface 14 of the first graft member 12. Free end 24 of connecting member 22 may be bonded to the first graft member 12 with an adhesive, e.g., Corethane®, or by any other means suitable for maintaining a fluid-tight seal. Connecting member 22 is pleated, and resides within the first graft member 12.

Various attachment configurations for connecting member 22 are contemplated. For example, connecting member 22 may be formed from graft material of the first graft member 12 and attached at a free end to the second graft member 20. Alternatively, connecting member 22 may be formed from a discrete segment of graft material, and attached at both free ends to the respective first and second graft members 12, 20. These alternative attachment configurations are not represented in the figures for clarity purposes.

FIG. 1A is a cross-sectional view of prosthesis 10 in a compressed configuration. More specifically, the pleats (also referred to as bellows) of connecting member 22 are compressed in an accordion-like fashion due to the coaxial positioning of the second graft member 20 relative to (and within) the first graft member 12, resulting in an axial length of prosthesis 10 of $L_C$. It is in this compressed configuration that prosthesis 10 is delivered to a desired location within a lumen.

The lumen within which prosthesis 10 is located typically undergoes a changing morphology, e.g., the lumen shrinks and/or kinks or straightens. The compressibility and expandability of connecting member 22 facilitates engagement of the second graft member 20 within the first graft member 12 to accommodate such a changing morphology, while maintaining a seal between the graft members 12, 20. In other words, in response to the changing morphology of the lumen, the graft members 12, 20 slide or telescope relative to one another, thereby varying the axial length of prosthesis 10.

FIG. 1B illustrates prosthesis 10 in an expanded configuration. More specifically, the pleats of connecting member 22 are expanded in an accordion-like fashion due to the coaxial positioning of the second graft member 20 relative to (and within) the first graft member 12, resulting in an axial length of prosthesis 10 of $L_E$. Because connecting member 22 is attached at one end to the first graft member 12 and attached at another end to the second graft member 20, a fluid-tight seal is maintained between the graft members 12, 20.

The representations of compressed axial length $L_C$ and expanded axial length $L_E$ in FIGS. 1A and 1B, respectively, are for illustrative purposes only. It is contemplated that the axial length of prosthesis 10 will vary, as necessary, to accommodate changing lumen morphology, constrained only by the compression and expansion limits of connecting member 22.

An exemplary material for forming graft members 12, 20 (and consequentially connecting member 22) is a synthetic polyester textile fiber. The present invention, however, is not limited to synthetic polyester textile fiber, and may include expanded polytetrafluoroethylene, or any other material that offers the desired fluid-tight sealing feature of connecting member 22.

Figures 2A, 2B:
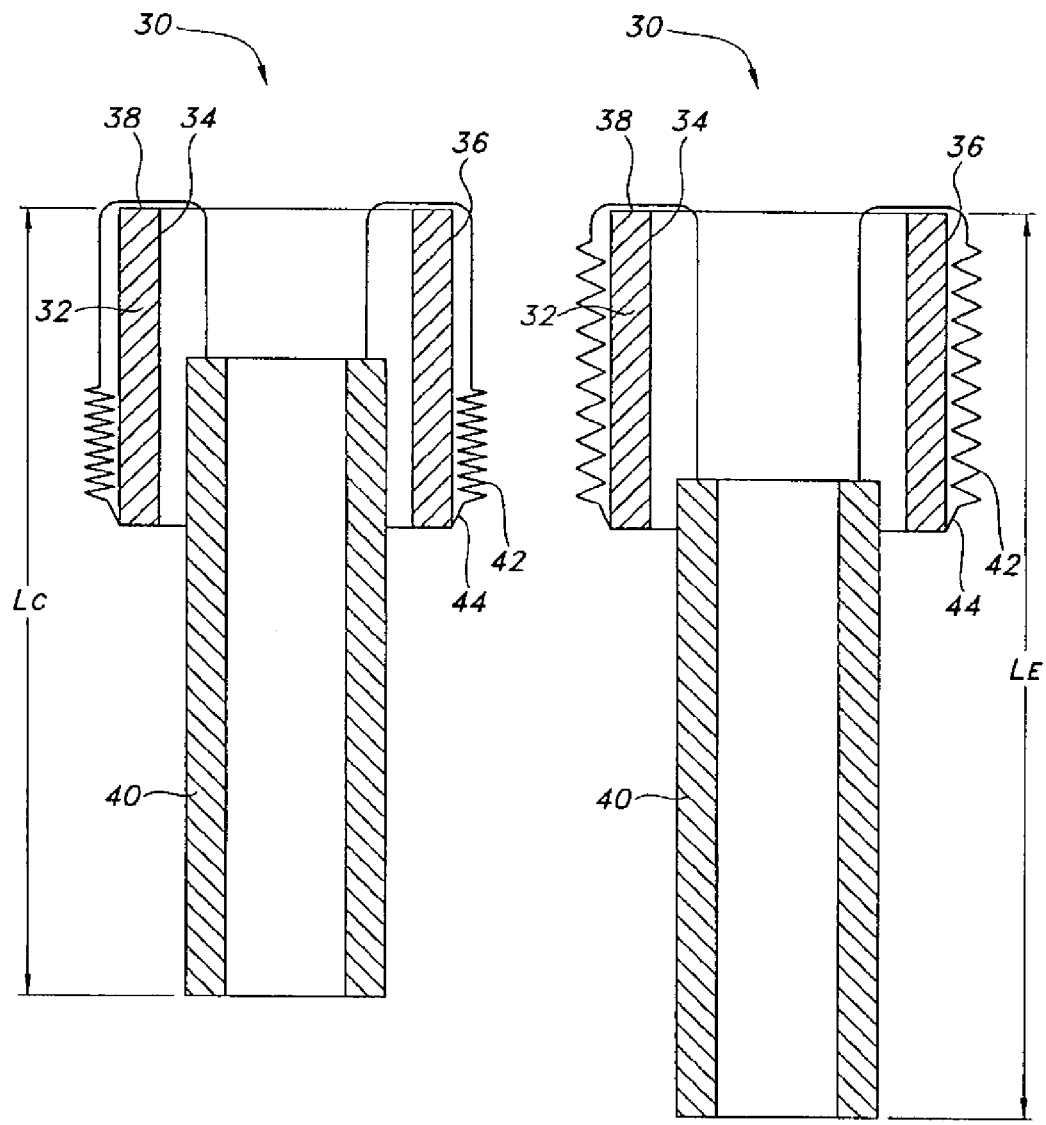
FIG. 2A is a cross-sectional view of another endovascular prosthesis in a compressed configuration, illustrating a pleated connecting member folded over a proximal end of a first graft member.
FIG. 2B is a cross-sectional view of the embodiment illustrated in FIG. 2A, showing the endovascular prosthesis in an expanded configuration.

FIGS. 2A and 2B illustrate another embodiment of a variable length endovascular prosthesis 30 adapted to prevent endoleaks. Similar to prosthesis 10 illustrated in FIGS. 1A and 1B, prosthesis 30 includes a substantially tubular first graft member 32 having an interior surface 34, an exterior surface 36, and a proximal end 38, and a substantially tubular second graft member 40 engaged coaxially within the first graft member 32. Prosthesis 30 further includes a substantially tubular fluid-tight connecting member 42 attached at one end to the first graft member 32 and attached at another end to the second graft member 40. Pleated connecting member 42 is axially compressible and expandable to facilitate engagement of the second graft member 40 within the first graft member 32 while maintaining a seal between the graft members 32, 40.

The configuration and operation of prosthesis 30 are essentially the same as those of prosthesis 10, described above with reference to FIGS. 1A and 1B. A notable difference, however, is the configuration of connecting member 42 in relation to the second graft member 40. More specifically, connecting member 42 is attached at a free end 44 to exterior surface 36 of the first graft member 32. As illustrated in FIGS. 2A and 2B, connecting member 42 folds over proximal end 38 of the first graft member 32.

FIG. 2A illustrates prosthesis 30 in a compressed configuration, and FIG. 2B illustrates prosthesis 30 in an expanded configuration.

Figure 3A:
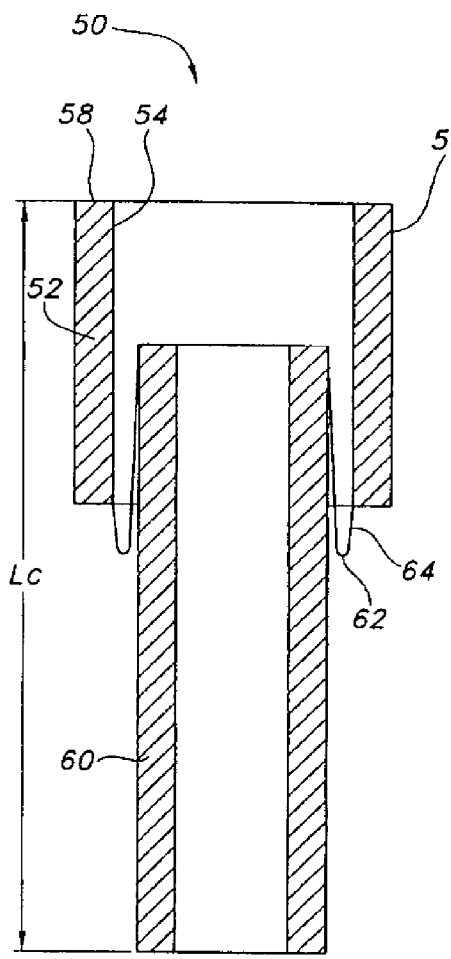
FIG. 3A is a cross-sectional view of yet another endovascular prosthesis in a compressed configuration, illustrating a substantially flat connecting member.
Figure 3B:
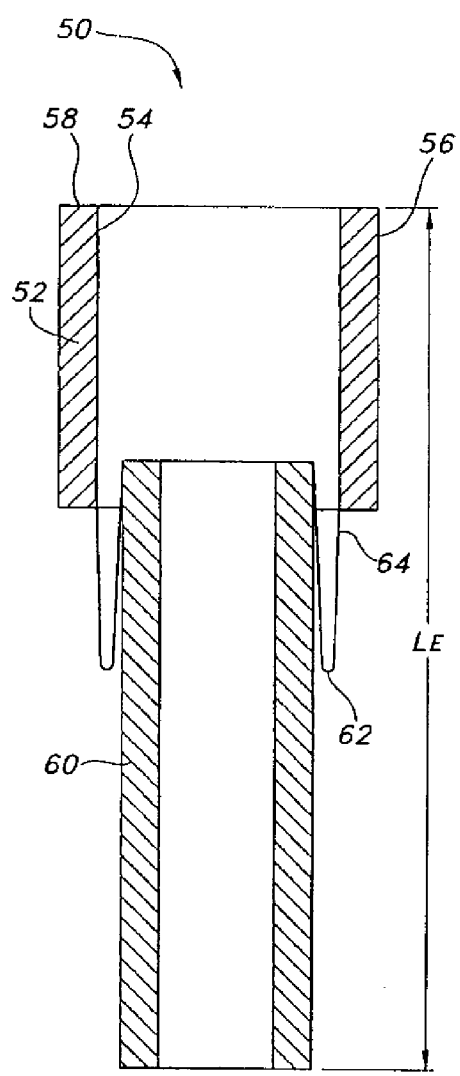
FIG. 3B is a cross-sectional view of the embodiment illustrated in FIG. 3A, showing the endovascular prosthesis in an expanded configuration.

FIGS. 3A and 3B illustrate yet another embodiment of a variable length endovascular prosthesis 50 adapted to prevent endoleaks. Similar to prosthesis 10 illustrated in FIGS. 1A and 1B, prosthesis 50 includes a substantially tubular first graft member 52 having an interior surface 54, an exterior surface 56, and a proximal end 58, and a substantially tubular second graft member 60 engaged coaxially within the first graft member 52. Prosthesis 50 further includes a substantially tubular fluid-tight connecting member 62 attached at one end to the first graft member 52 and attached at another end to the second graft member 60. Connecting member 62 is axially compressible and expandable to facilitate variable length of telescoping engagement of the second graft member 60 within the first graft member 52 while maintaining a seal between the graft members 52, 60.

The configuration and operation of prosthesis 50 are essentially the same as those of prosthesis 10, described above with reference to FIGS. 1A and 1B. A notable difference, however, is the shape of connecting member 62 and its configuration in relation to the second graft member 60. More specifically, connecting member 62 is substantially flat, and is attached at a free end 64 to interior surface 54 of the first graft member 52. As illustrated in FIGS. 3A and 3B, connecting member 62 hangs between the first and second graft members 52, 60.

FIG. 3A illustrates prosthesis 50 in a compressed configuration, and FIG. 3B illustrates prosthesis 50 in an expanded configuration.

The construction of variable length endovascular prostheses 10, 30, 50 is not limited to graft material. More specifically, prostheses 10, 30, 50 may include, for example, a substantially tubular first stent-graft 12, 32, 52, respectively, and a substantially tubular second stent-graft 20, 40, 60, respectively, engaged coaxially within first stent-graft 12, 32, 52, respectively. The endovascular prosthesis of the present invention may include two graft members constructed of graft material, two graft members constructed of stent-grafts, or a combination thereof.

The configuration and operation of these alternative embodiments are essentially the same as those described above with reference to FIGS. 1A-3B. The construction of the stents of stent-grafts 12, 20, 32, 40, 52, 60 may be of any type of self-expanding or balloon-expandable stent.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. A variable length endovascular prosthesis adapted to prevent endoleaks, said prosthesis comprising:
   a substantially tubular first graft member comprising an interior surface, an exterior surface, and an open end;
   a substantially tubular second graft member engaged coaxially within said first graft member, the second graft member having a proximal end; and
   a substantially tubular fluid-tight connecting member having two axially separated ends that is attached at one end to said first graft member and attached at another end to a cross-sectional edge at said proximal end of said second graft member,
   wherein said one end is attached to either said interior surface or said exterior surface of said first graft member, and
   wherein said connecting member is axially compressible and expandable in response to movement of said second graft member and wherein a length of said connecting member is variable and a length of said second graft member is maintained to facilitate engagement of said proximal end of said second graft member within said first graft member while maintaining a seal between said proximal end of said second graft member and said open end of said first graft member.

2. The prosthesis of claim 1, wherein said connecting member comprises graft material.

3. The prosthesis of claim 1, wherein said connecting member is formed from graft material of said second graft member and is attached at a free end to said first graft member.

4. The prosthesis of claim 1, wherein a length of said first graft member is maintained.

5. The prosthesis of claim 1, wherein said connecting member partially resides within said first graft member.

6. The prosthesis of claim 3, wherein said free end of said connecting member is attached to said exterior surface of said first graft member.

7. The prosthesis of claim 6, wherein said connecting member folds over said open end of said first graft member.

8. The prosthesis of claim 1, wherein said connecting member is at least partially pleated.

9. The prosthesis of claim 1, wherein said connecting member is substantially flat.

10. The prosthesis of claim 1, wherein said first graft member comprises a first stent-graft.

11. The prosthesis of claim 1, wherein said second graft member comprises a second stent-graft.

12. The prosthesis of claim 1, wherein said first graft member and said second graft member are formed from graft material, or said first graft member and said second graft member comprise separate stent-grafts, or a combination thereof.

13. A method of providing a variable length tubular endovascular prosthesis, said method comprising:
   attaching a substantially tubular fluid-tight connecting member, having two axially separated ends, at one end to a substantially tubular first graft member comprising an interior surface, an exterior surface, and an open end, wherein said one end is attached to either said interior surface or said exterior surface of said first graft member;
   attaching the connecting member at another end to a cross-sectional edge at a proximal end of a substantially tubular second graft member engaged coaxially within the first graft member;
   said connecting member being axially compressible and expandable in response to movement of said second graft member and wherein a length of said connecting member is variable and a length of said second graft member is maintained so as to facilitate engagement of said proximal end of the second graft member within the first graft member; and
   maintaining a seal between the proximal end of the second graft member and the open end of the first graft member.

14. The method of claim 13, further comprising:
   forming the connecting member from graft material of the second graft member; and
   attaching the connecting member at a free end to the first graft member.

15. The method of claim 14, further comprising configuring a length of the first graft member to be maintained.

16. The method of claim 15, further comprising partially residing the connecting member within the first graft member.

17. The method of claim 16, further comprising attaching the free end of the connecting member to the exterior surface of the first graft member.

18. The method of claim 17, further comprising folding the connecting member over the open end of the first graft member.

19. The method of claim 13, further comprising deploying the endovascular prosthesis in a radially compressed configuration endoluminally in a body lumen that is subject to possible morphological changes, wherein variations in a total length and shape of the endovascular prosthesis in a radially decompressed configuration contribute to maintaining the seal in order to prevent endoleaks.

20. A variable length endovascular prosthesis adapted to prevent endoleaks, said prosthesis comprising:
   a substantially tubular first graft member, comprising an interior surface, an exterior surface, and an open end;
   a substantially tubular second graft member engaged coaxially within said first graft member, the second graft member having a proximal end; and
   a means having two axially separated ends for permitting axial compression and expansion of said prosthesis in response to movement of said second graft member and wherein a length of said second graft member is maintained to facilitate variable length engagement of said second graft member within said first graft member while maintaining a seal between said graft members, wherein at least a portion of the means for permitting axial compression and expansion of said prosthesis resides within said first graft member with one end that is attached to either said interior surface or said exterior surface of said first graft member and another end that is attached to a cross-sectional edge at said proximal end of said second graft member.

21. The prosthesis of claim 20, wherein said means for axially compressing and expanding said prosthesis comprises a substantially tubular fluid-tight connecting member attached at said one end to said first graft member and attached at said another end to said second graft member.

22. The prosthesis of claim 20, wherein said open end of said first graft member and said proximal end of said second graft member provide an opening between said first and second graft members at an opposing end of said first graft member.

* * * * *